United States Patent
Conio et al.

(10) Patent No.: US 8,946,502 B2
(45) Date of Patent: *Feb. 3, 2015

(54) SLIGHT-INCONTINENCE SANITARY NAPKIN STRUCTURE

(75) Inventors: Guido Conio, Lacchiarella (IT); Giorgio Mantovani, Lacchiarella (IT)

(73) Assignee: Corman S.p.A., Lacchiarella (MI) (IT)

( * ) Notice: Subject to any disclaimer, the term of this patent is extended or adjusted under 35 U.S.C. 154(b) by 358 days.

This patent is subject to a terminal disclaimer.

(21) Appl. No.: 12/924,485

(22) Filed: Sep. 28, 2010

(65) Prior Publication Data

US 2011/0077607 A1 Mar. 31, 2011

(30) Foreign Application Priority Data

Sep. 29, 2009 (IT) ............................... MI2009A1663

(51) Int. Cl.
*A61F 13/15* (2006.01)
(52) U.S. Cl.
USPC ............... 604/384; 604/385.01; 604/385.101; 604/377; 604/378; 604/367; 604/368; 604/374
(58) Field of Classification Search
USPC ............. 604/384, 385.01, 385.101, 377, 378, 604/367, 368, 374
See application file for complete search history.

(56) References Cited

U.S. PATENT DOCUMENTS

| 4,235,237 | A | 11/1980 | Mesek | |
|---|---|---|---|---|
| 4,333,462 | A | 6/1982 | Holtman | |
| 4,333,463 | A | 6/1982 | Holtman | |
| 5,607,414 | A | 3/1997 | Richards | |
| 2001/0025162 | A1* | 9/2001 | Roe et al. | 604/364 |
| 2004/0166307 | A1* | 8/2004 | Tamburro et al. | 428/327 |
| 2007/0142803 | A1* | 6/2007 | Soerens et al. | 604/368 |

FOREIGN PATENT DOCUMENTS

| EP | 0 063 331 | 10/1982 |
|---|---|---|
| EP | 0 108 637 | 5/1984 |
| EP | 0 122 042 A2 | 10/1984 |
| WO | WO91/11165 | 8/1991 |
| WO | WO94/28838 | 12/1994 |
| WO | WO2006/039307 A2 | 4/2006 |

* cited by examiner

*Primary Examiner* — Jacqueline F. Stephens
(74) *Attorney, Agent, or Firm* — Hedman & Costigan, P.C.; James V. Costigan; Kathleen A. Costigan

(57) ABSTRACT

A sanitary napkin structure, particularly for a slight incontinence, said sanitary napkin structure comprising a first substantially permeable sheet, a second substantially impermeable sheet and an absorbing pad enclosed between said first and second sheets, characterized in that said absorbing pad comprises an absorbing pad layer including a flexible cotton fiber and a superabsorbing polymer matrix, wherein the cotton fibers in said matrix have a random orientation along three axes and do not have a preferential orientation in a X-Y plane.

11 Claims, 1 Drawing Sheet

SLIGHT-INCONTINENCE SANITARY NAPKIN STRUCTURE

BACKGROUND OF THE INVENTION

The present invention relates to a slight-incontinence sanitary napkin structure.

As is known, the so-called SAP or superabsorbent polymer, is a polymeric material designed and suitable for absorbing great amounts of fluids and to hold them under comparatively low pressures, thereby this material is very useful for making absorbing structures or constructions for incontinence sanitary products.

The above polymer and the absorbing products obtained thereby, have been already disclosed in prior U.S. patents, such as U.S. Pat. No. 3,669,103 to Harper and U.S. Pat. No. 3,670,731 to Harmon.

The absorption capability and efficiency of SAP in disposable absorbing products greatly depend on the shapes, positions and manners by which SAP is embedded in the end product.

In some cases, i.e. as the SAP density is a comparatively high one, its efficiency may be negatively affected by the so-called gel-blocking phenomenon, which term means a condition which is achieved as the SAP is in a wet condition, and inflates and prevents liquids from arriving at inner parts of the absorbing products.

In actual practice, the fluid absorption occurs with an absorption rate much lower than the fluid releasing rate from the human body, thereby causing excessive fluid losses, without fully saturating the absorbing article SAP material, said gel-blocking phenomenon increasing as the SAP density increases.

On the other hand, a high SAP concentration would be very desirable to achieve a sufficient absorbing capability of the absorbing article or product.

Several attempts to improve the fluid absorbing efficiency of SAP materials, by reducing the above gel-blocking phenomena, are extensively disclosed in the literature.

For example, Weisman and Goldman (EP-122042), disclose an absorbing structure wherein SAP is dispersed through a hydrophilic fiber airlaid layer, compressed to set density.

Buttherworth (U.S. Pat. No. 4,235,237) discloses an absorbing article including absorbing material particles spaced from one another within the article structure.

Mazurak (EP-0063331) discloses an absorbing article containing a mixture of SAP and a filling material processed by a surface active agent.

Further prior documents disclose the arrangement of SAP materials within different absorbing article.

The EP-122042 patent discloses that a SAP containing layer may be arranged at the bottom of an absorbing article having its top part contacting the human body and comprising hydrophilic fibers only.

The U.S. Pat. No. 4,333,463 and U.S. Pat. No. 4,333,462 to Holtman disclose an absorbing article containing an amount of superabsorbing particles arranged near an end portion of the absorbing article.

Further attempts for improving SAP materials to limit the mentioned gel-blocking phenomenon have been further made and disclosed in yet other prior documents, and are mainly based on methods for allowing SAP to hold a spherical shape in a wet condition, that is to leave interstitial free spaces or cells allowing fluids to enter the core of the absorbing article.

The PCT application WO2004/096303 to Frank and Qin discloses polymers having an improved strength under a pressure condition and holding a set spherical shape, for making improved absorbing articles.

It should be pointed out that, to achieve an optimum performance in slight incontinence sanitary articles, it would be necessary to consider a further very important parameter, in addition to the article absorbing capability, that is the article body fluid absorbing rate.

In fact, an urine jet of a slightly incontinent person corresponds to a small urine amount, but with a comparatively high flow rate, since an urine loss is an event in which the incontinent person temporarily loses his/her control, typical for example because of a sneezing, laughing or an physical effort.

Thus, in slight-incontinence articles, the article absorbing rate or speed is much more important than the absorbing capability.

An increase of the absorbing capability, even if always desirable, would not be sufficient, per se, to provide a good urine absorbing performance.

Several methods for increasing the urine or fluid absorbing rate, without reducing the amount of superabsorbing polymer and holding a high absorbing power are always known, in which multi-layer structures including absorbing cores made of cellulose fibers in which the superabsorbing polymer is embedded are used.

In these structures the liquid is conveyed through the article by capillarity, the cellulose fibers operating as a vehicle to arrive at the superabsorbing polymer.

As stated, the gel-blocking phenomenon negatively affects the capillarity liquid spreading.

To overcome the above limitation, an approach would be that of using an additional absorbing layer added to the so-called "spreading or absorbing" pad, as disclosed by Pleniak in the EP-108637 patent.

Generally, this absorbing layer would comprise processed cellulose fibers, as disclosed by Cook in the PCT Patent Application WO91/11165, or a non woven fabric material, as disclosed, for example, by Palumbo and Carlucci in the PCT Patent Application WO9428838 and by Richards in the U.S. Pat. No. 5,607,414, in which no superabsorbing polymer or very small amount thereof is used.

Waksmundzki discloses in his PCT Patent Application WO2006/039307, superabsorbing polymer multilayer fluid absorbing articles.

With reference to FIG. 1 a conventional absorbing pad structure is herein shown comprising a liquid receiving layer 1, devoid of superabsorbing polymers, for quickly drawing and spreading the liquid, and an underlying pad layer 2 including a superabsorbing polymer, is arranged between two sheet elements, of which a first sheet element 3 is permeable to the liquids and contacts the body of the user and the second sheet element 4, impermeable to the fluids, faces the user garments.

Thus, in this prior structure the first layer has only a liquid drawing and non absorbing function, with the drawback that it remains wet and contacts the user skin, thereby irritating it.

A further desirable characteristic of an absorbing article, also very important for the liquid absorbing power thereof, is that of holding an integral condition with the article in a wet condition.

This may be achieved as follows:

(a) binding with one another the fibers of the absorbing layer by chemical or mechanical methods, which methods, however, make the absorbing pad much more hard thereby reducing the user comfort;

(b) using fibers of a greater average length and so braided or entangled to form a very firm or solid fiber network.

Cotton, which has very long fibers, is very suitable to form the above braided and strong constructions.

However, cotton is scarcely broadly used in absorbing products because of its high cost, larger than that of a wood cellulose fiber.

Typical absorbing structures of a cotton material could be made by overlapping multiple layers of textile fiber webs, from a carding process and blowing or suction methods, and then pressing said layers to increase the fiber cohesion, thereby the made article will comprise "combed" fibers oriented in the article longitudinal direction, and which will preferably convey the fluid through a X-Y plane and not in a depth direction.

SUMMARY OF THE INVENTION

Accordingly, the aim of the present invention is to overcome the above mentioned drawbacks of prior slight incontinence sanitary napkin structures or articles.

Within the scope of the above mentioned aim, a main object of the invention is to provide such a slight-incontinence sanitary napkin structure adapted to quickly absorb liquids and control high liquid flow articles.

Another object of the present invention is to provide such an absorbing structure or article having an absorbing capability or power sufficient to collect a comparatively high amount of liquids (multiple liquids loads).

Another object of the invention is to provide such an absorbing structure, in particular for slight-incontinence applications, adapted to remain integral notwithstanding repeated mechanical stresses it is subjected to, for example due to movements of the user legs and repeated urine absorptions.

Another object of the invention is to provide such a fluid absorbing structure or article preventing the user skin from being irritated.

According to one aspect of the present invention, the above mentioned aim and objects, as well as yet other objects, which will become more apparent hereinafter, are achieved by a sanitary napkin structure, particularly for a slight incontinence, said sanitary napkin structure comprising a first substantially permeable sheet, a second substantially impermeable sheet and an absorbing pad enclosed between said first and second sheets, characterized in that said absorbing pad comprises an absorbing pad layer including a flexible cotton fiber and a superabsorbing polymer matrix, wherein the cotton fibers in said matrix have a random orientation along three axes and do not have a preferential orientation in a X-Y plane.

The absorbing product structure or article according to the invention is characterized by an improved fluid absorbing rate, which is achieved without limiting the overall absorbing capability of the product itself.

BRIEF DESCRIPTION OF THE DRAWINGS

Further characteristics and advantages of the present invention will become more apparent hereinafter from the following detailed disclosure of a preferred, though not exclusive, embodiment of the invention, which is illustrated, by way of an indicative, but not limitative, example in the accompanying drawings, where.

DESCRIPTION OF THE PREFERRED EMBODIMENTS

Figure 1:
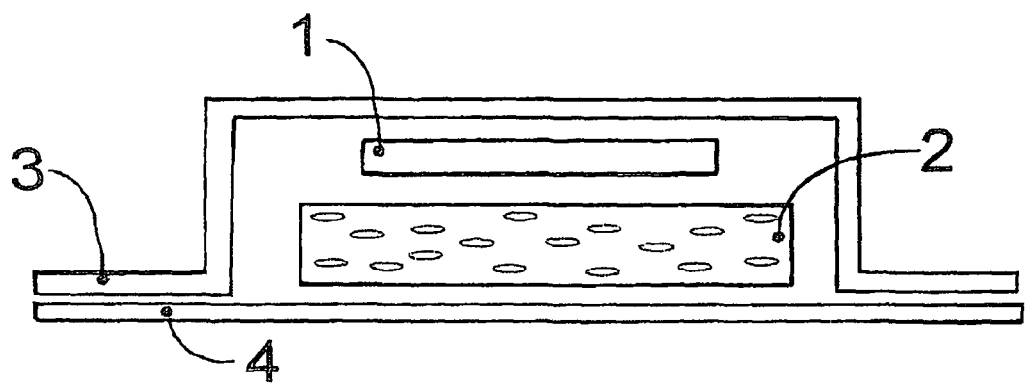
FIG. 1 is a cross-sectional view of an absorbing structure or article comprising an absorbing pad including cellulosic or synthetic fibers mixed with a superabsorbing polymer and with an overlapping liquid acquisition or absorbing and distributing layer.

With reference to the number references of the above mentioned figures, the absorbing sanitary napkin structure, specifically designed for slight incontinence applications, according to the present invention, comprises a first substantially permeable sheet 3, a second substantially impermeable sheet 4, and an absorbing pad 1, 2 enclosed between said first and second sheets 3, 4.

Said absorbing pad comprises a natural cotton fiber mixture, the fibers of which are randomly oriented through a 3D structure, and, accordingly, do not have a preferential orientation in a X-Y plane, said fibers being mixed with a superabsorbing polymer matrix.

Since cotton has a very high capillarity, it is not affected by the above mentioned gel-blocking effect, at the SAP rates which will be hereinbelow defined.

The orientation of the cotton fibers along the axis Z too, allows a fluid to be conveyed to the innermost layers of the product, thereby actually spreading it through the three Cartesian axes.

Owing to the above improved fluid conveying capability, an additional amount of absorbing material may also be added under the core of the product, thereby allowing to reduce the SAP density in the cotton core.

This, together with the use of a truly natural material such as cotton, which does not generate sensitization phenomena, will mitigate a possible user skin reddening or rushing.

Moreover, the cotton fibers, which, as is well known, have a comparatively long length and are mutually entangled, provide the absorbing product with a firm structure while preserving its desirable properties even after repeated fluid loads.

Thereinbelow some terms which will be used in the following disclosure and the meanings thereof will be defined.

The term "Z dimension" or "Z axis" relates to a dimension orthogonal to the plane defined by the product length and width. The Z axis usually corresponds to the thickness of the layer, structure or product.

The term "X-Y dimension" or "X-Y plane" relates to the plane defined by the product length and width.

The term "non woven" or "non woven fabric" relates to a fabric material having a composite structure including individual inter-braided fibers with a repeating pattern, and not to a non woven product.

This is achieved by several methods, such as, for example, melt blowing, spun bonding and carding processes.

The term "particle" or "grain" related to a material including a plurality of very small discrete units, such as powders, balls and particle material.

The grain may have any desired shape such as, for example, a cubic, cylindric, polyhedric, spherical or semispherical, uneven shape, or any desired combinations of these shapes.

Grain shapes having a dimension much greater than the other, such as a needle, thread, fiber are included in such a definition.

The target particle may be moreover coated by a gel, film, protein or the like and may have a core particle, or it may be uncoated.

The term "particle" may comprise moreover an agglomerate, that is may include more than a single grain, particle or the like, The term "superabsorbing" or "SAP" or "polymer" relates to an absorbing material capable of absorbing and holding at least 10 grams of an aqueous liquid (such as water, a saline solution or synthetic urine, such as, for example, the product K-C 399105 of the PPG Company) for each gram of absorbing material as immersed into the liquid for four hours and upon pressing to 0.5 psi.

The term "cotton" or "cotton fibers" relates to fibers made from cotton seeds or a mixture thereof with any other desired fibers, provided that the cotton fibers are present in a prevailing amount.

The subject matter of the present invention is a disposable or single-use article capable of absorbing large amounts of body fluids, such as menstrual fluids, urine, sweats, feces.

Thus, this article may be in the form of a woman or child sanitary napkin structure, an incontinent person product and the like.

While in the following disclosure reference will be made to a preferred slight incontinence product, it should be apparent that the disclosure could be extended to any other product forms adapted to absorb body fluids.

The disposable sanitary napkin products usually comprise three basic structural components.

A sheet element 4, shown in FIG. 1, consists of an impermeable or substantially impermeable sheet, which is conventionally called "backsheet".

On the top of this impermeable sheet an absorbing component is arranged, comprising the elements shown by the reference numbers 1 and 2, said absorbing component conventionally comprising two or more layers.

This absorbing component is generally called the "pad".

On the top of this component, a water permeable or substantially permeable sheet 3, the so-called "topsheet" is arranged.

The pad according to the present invention comprises at least an absorbing layer including a cotton fiber flexible matrix.

These cotton fibers, being much more longer than cellulosic fibers included in conventional products, will provide a much more entangled resilient and resistant matrix, in particular in a wet condition thereof.

The matrix may have a basis weight preferably from 50 to 1000 grams/m$^2$ (gsm), from 100 to 800 gsm and most preferably from 150 to 600 gsm.

As stated, the fibers are arranged with a 3D random arrangement, and no preferential axis exists.

According to a further embodiment of the invention, the cotton fiber matrix is characterized by a basis weight varying along the X-Y plane, thereby providing the so-called "3D core".

In the preferred embodiment of the invention, the central region of the product has a greater basis weight, whereas the product peripheral regions are characterized by a smaller basis weight.

This structure has been designed for concentrating the product absorbing capability at the regions where it is actually necessary, and for providing the product with a more ergonomic shape.

In other embodiments, the high and low basis weight regions may be differently arranged.

The cotton fiber matrix comprises, embedded in its inside, at interstices left free from the fiber network, superabsorbing particles.

The amount of superabsorbing particles embedded in the matrix will depend on the cotton fiber amount and may vary from 5% to 70% of the total weight of the cotton fiber matrix and superabsorbing particle assembly.

More preferably, said amount or rate may vary from 10% to 50% and most preferably from 15% to 40%.

Preferably, said superabsorbing particles are homogeneously mixed with the cotton fibers and accordingly they will be present in a higher amount where the cotton fiber matrix basis weight is greater.

According to a less preferred embodiment, the distribution of the superabsorbing polymer will be fully independent from the cotton fiber matrix structure.

Figure 2:
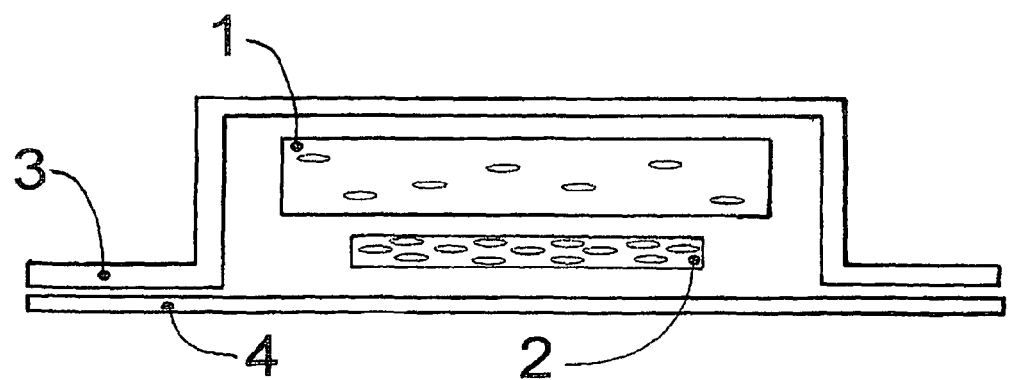
FIG. 2 is a cross-sectional view of a preferred embodiment of the absorbing structure, according to the present invention, including an absorbing pad comprising a cotton matrix and a superabsorbing polymer, with a further layer consisting of cellulosic fibers and a superabsorbing polymer.

In a further embodiment, the pad may comprise a further layer arranged toward the backsheet 2 of FIG. 2, that is at a larger distance from the permeable side than the cotton fiber and superabsorbing particle matrix.

The further layer has a function of providing an additional absorbing capability or power and will collect all those fluids coming from the top layers, owing to an enhanced flow along the Z axis, and which fluid would not have been absorbed during such a path.

Said layer may comprise, in turn, different fiber material layers, containing superabsorbing particles.

These materials may comprise, without any limitation, a plurality of "airlaid" multilayers, including polyester (PET) fibers, polypropylene (PP) fibers, two-component fibers, cellulose fibers optionally chemically modified and optional amulsions thereof.

The superabsorbing particles will be preferably present in a rate larger than that of the overlaying layers.

In a second embodiment of the invention, the layer may comprise only superabsorbing particles glued thereto or bound thereto by any other suitable material for containing and stabilizing the grains on the backsheet.

In yet another embodiment, the profile contour of the cotton matrix on the X-Y plane will be preferably a contour tapering to the structure center, in a so-called typical hourglass shape, or at one end portion thereof.

This configuration will provide the product with an anatomic contour of facilitated use.

The cotton fiber matrix according to the present invention allows to achieve the mentioned anatomic shape without using additional process steps after forming the pad, which would negatively affect the softness of the products as well as its capability of reducing irritation phenomena.

Actually, the above processes, usually of a cutting mechanic type, would increase the hardness of the product contour, thereby greatly reducing its comfort.

It has been found that the invention fully achieved the intended aim and objects.

In fact, the invention provides an absorbing structure which is very advantageous and improved with respect to like commercially available products.

In practicing the invention, the used materials, as well as the continent size and shapes, can be any, according to requirements.

The invention claimed is:

1. A sanitary napkin structure, particularly for a slight incontinence, said sanitary napkin structure comprising a first substantially permeable sheet, a second substantially impermeable sheet and an absorbing pad enclosed between said first and second sheets, characterized in that said absorbing pad comprises an absorbing pad layer consisting of a flexible cotton fiber and superabsorbing polymer matrix, wherein the cotton fibers have a random orientation along three axes and do not have a preferential orientation in a X-Y plane, and wherein said napkin structure has a central region having a basis weight greater than a basis weight of peripheral regions of said napkin structure thereby concentrating an absorbing capability of said napkin structure at set regions of said structure while providing said structure with improved ergonomic characteristics.

2. A sanitary napkin structure, according to claim 1, characterized in that said flexible cotton fiber matrix has an X-Y plane variable basis weight ranging from 50 to 1,000 grams/$m^2$.

3. A sanitary napkin structure, according to claim 2, characterized in that said flexible cotton fiber matrix has an X-Y plane variable basis weight changing from 100 to 800 grams/$m^2$.

4. A sanitary napkin structure, according to claim 2, characterized in that said flexible cotton fiber matrix has an X-Y plane variable basis weight changing from 150 to 600 grams/$m^2$.

5. A sanitary napkin structure, according to claim 1, characterized in that said cotton matrix has in a X-Y plane a profile tapering in a longitudinal direction, or with width variations along its longitudinal axis.

6. A sanitary napkin structure, according to claim 1, characterized in that said cotton matrix is blended with superabsorbing polymer particles, being included in a rate from 5% to 70% based on a total weight of said cotton and polymer matrix, said particles being homogeneously mixed with cotton fibers and present in a higher amount where the cotton fiber matrix basis weight is greater.

7. A sanitary napkin structure, according to claim 6, characterized in that said cotton matrix is blended with superabsorbing polymer particles, being included in a rate from 10% to 80%, said particles being homogeneously mixed with cotton fibers and present in a higher amount where the cotton fiber matrix basis weight is greater.

8. A sanitary napkin structure, according to claim 1, characterized in that said cotton matrix is blended with superabsorbing polymer particles, being included in a rate from 15% to 40%, said particles being homogeneously mixed with cotton fibers and present in a higher amount where the cotton fiber matrix basis weight is greater.

9. A sanitary napkin structure, according to claim 1, characterized in that said pad has an additional absorbing layer arranged between a main layer and the water impermeable sheet, consisting of an airlaid pattern including superabsorbing polymer particles in a rate by weight larger than that of said main layer.

10. A sanitary napkin structure, according to claim 1, characterized in that said structure comprises a perspiring backsheet.

11. A sanitary napkin structure, according to claim 1, characterized in that said structure comprises a topsheet mainly consisting of cotton.

* * * * *